(12) United States Patent
Roberts et al.

(10) Patent No.: US 9,248,244 B2
(45) Date of Patent: Feb. 2, 2016

(54) SAFETY DEVICE AND INJECTION DEVICE

(75) Inventors: Gareth Roberts, Wrexham (GB); John Slemmen, Mereyside (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 74 days.

(21) Appl. No.: 13/977,943

(22) PCT Filed: Dec. 30, 2011

(86) PCT No.: PCT/EP2011/074278
§ 371 (c)(1),
(2), (4) Date: Jul. 2, 2013

(87) PCT Pub. No.: WO2012/093073
PCT Pub. Date: Jul. 12, 2012

(65) Prior Publication Data
US 2013/0289481 A1 Oct. 31, 2013

(30) Foreign Application Priority Data

Jan. 4, 2011 (EP) .................................... 11150081

(51) Int. Cl.
*A61M 5/32* (2006.01)
*A61M 5/28* (2006.01)

(52) U.S. Cl.
CPC ............ *A61M 5/3221* (2013.01); *A61M 5/326* (2013.01); *A61M 5/3287* (2013.01); *A61M 5/28* (2013.01); *A61M 5/3204* (2013.01); *A61M 2005/3247* (2013.01)

(58) Field of Classification Search
CPC ............ A61M 5/2026; A61M 5/2033; A61M 5/3245; A61M 5/3257; A61M 5/326; A61M 5/31578; A61M 2005/3261; A61M 2005/3264; A61M 2005/3265; A61M 2005/3267; A61M 2005/3268

USPC ........... 604/110, 134, 135, 136, 164.08, 187, 604/197, 198
See application file for complete search history.

(56) References Cited

U.S. PATENT DOCUMENTS 6,852,096 B1* 2/2005 Pouget ................ A61M 5/3257
604/110
2003/0144631 A1* 7/2003 Doyle ................ A61M 5/3243
604/198

(Continued)

FOREIGN PATENT DOCUMENTS

EP 1970086 9/2008
FR 2799975 4/2001

(Continued)

OTHER PUBLICATIONS

International Search Report for Int. App. No. PCT/EP2011/074278, completed Apr. 18, 2012.

*Primary Examiner* — Nicholas Lucchesi
*Assistant Examiner* — Justin L Zamory
(74) *Attorney, Agent, or Firm* — Fish & Richardson P.C.

(57) ABSTRACT

According to the invention, a safety device for a pre-filled syringe comprises of a needle shield adapted to cover an injection needle of the pre-filled syringe before and after an injection, a support body with at least one pivoting arm adapted to engage a barrel collar of the pre-filled syringe and an outer body with a first inner sleeve comprising a bevelled section. The needle shield, the support body and the outer body are telescopically arranged. The needle shield, the support body and the outer body may telescope with respect to each other to cover and to expose the injection needle of the pre-filled syringe. The bevelled section is arranged to abut against the pivoting arm connected to the support body by a living hinge to deflect the pivoting arm radially inwards, so that the pivoting arm may engage the barrel collar after a dose of a medicament contained in the pre-filled syringe has been disposed beneath the skin of a patient receiving the injection.

11 Claims, 8 Drawing Sheets

(56) References Cited

U.S. PATENT DOCUMENTS

2003/0144632 A1 7/2003 Hommann et al.
2005/0277894 A1* 12/2005 Westbye ............. A61M 5/1782
604/198

FOREIGN PATENT DOCUMENTS

| WO | 2006/111862 | 10/2006 |
| WO | 2007/047200 | 4/2007 |
| WO | 2010/104779 | 9/2010 |

* cited by examiner

SAFETY DEVICE AND INJECTION DEVICE

CROSS REFERENCE TO RELATED APPLICATIONS

The present application is a U.S. National Phase Application pursuant to 35 U.S.C. §371 of International Application No. PCT/EP2011/074278 filed Dec. 30, 2011, which claims priority to European Patent Application No. 11150081.5 filed Jan. 4, 2011. The entire disclosure contents of these applications are herewith incorporated by reference into the present application.

TECHNICAL FIELD

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety device known in the state of the art achieves the object of providing needle safety by arranging the pre-filled syringe movable relative to a body, where the pre-filled syringe is retracted into the body after the injection.

WO 2006/111862 A1 discloses an injection assistance device comprising a body with a needle, grasping means and first elastic return means to dampen limited movement of said grasping means, in at least one of the two directions, respectively distal or proximal, during an injection phase, and to maintain said body in its insertion position and said needle at a constant insertion length during the injection step, when the user increases, respectively releases, a distal pressure on the grasping means. WO 2006/111862 A1 also relates to an injection set comprising an injection device and the said assistance device.

FR 2 799 975 A1 discloses a disposable hypodermic syringe having a safety sleeve with a forward end in which a barrel can slide between an operating position with a needle holder deployed and a safety position with it retracted. The syringe has a telescopic head containing a spring which is released automatically at the end of the pressure stroke to retract the barrel and needle inside the sleeve. Disposable hypodermic syringe comprises a barrel, a needle holder, a plunger and a safety sleeve with a forward end in which the barrel can slide between an operating position with the needle holder deployed and a safety position with it is retracted. The syringe has a telescopic head containing a spring which is released automatically at the end of the pressure stroke to retract the barrel and needle inside the sleeve. Lugs inside the head hold the barrel in its retracted position and prevent re-use.

WO 2010/104779 A1 discloses a pharmaceutical delivery apparatus with an automatic syringe retraction following a manually controlled injection. The apparatus includes a housing, a syringe carriage, a medication-filled syringe held within the carriage, the syringe needle tip being disposed within the housing in a first position and projecting from the housing beyond the housing proximal end for insertion into an injection site in a second position, a manually shiftable plunger, means on the carriage and the housing and the plunger for causing the carriage to advance from the first position to the second position and for injecting medicine from the syringe when the plunger is manually plunged proximally toward the housing, and means on the carriage and the plunger for causing the carriage to retract from the second position to a position at which the needle tip is disposed within the housing when the plunger shifts distally.

EP 1 970 086 A2 discloses an injection device for use with a pre-filled syringe. The device features a track and track follower engagement which facilitates locking a protective needle guard over the tip of the needle at the conclusion of the injection. The device further includes a tamper evidence overcap which, once removed from the device cannot be readily reinstalled. The injection device features a tubular handle which is grasped by the hand and moved towards the injection site to administer the injection. The device is suitable for self-administration of injections.

WO 2007/047200 A1 discloses a pharmaceutical delivery apparatus including a housing, a syringe assembly, and a needle cap. The syringe assembly is plungeable relative to the housing from a first position, at which its needle tip is disposed within the housing, to a second position, at which its needle tip projects from the housing beyond the proximal end for insertion into an injection site. A base of the needle cap is exposed at the housing proximal end to be manually grippable for cap removal. A needle cap stem is upstanding from the base and sized and configured to insert through an opening is the housing proximal end to cover the needle tip when the syringe assembly is disposed in the first position. The needle cap base further includes a plurality of distally projecting cams located radially outward of the stem. The cams are fittable within slots in the housing proximal end when the cap is fully mounted to the apparatus.

SUMMARY

It is an object of the present invention to provide an improved safety device for a pre-filled syringe.

It is a further object of the invention to provide an improved injection device with a pre-filled syringe that is safe to handle and in particular prevents accidental needle stick injuries.

The object is achieved by a safety device according to claim 1 and by an injection device according to claim 6.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises a needle shield adapted to cover an injection needle of the pre-filled syringe before and after an injection, a support body with at least one pivoting arm adapted to engage a barrel collar of the pre-filled syringe and an outer body with a first inner sleeve comprising a bevelled section.

The needle shield, the support body and the outer body are telescopically arranged. The needle shield, the support body and the outer body may telescope with respect to each other to cover and to expose an injection needle of the pre-filled syringe during an injection. The bevelled section is arranged to abut against the pivoting arm connected to the support body by a living hinge to deflect the pivoting arm radially inwards, so that the pivoting arm may engage the barrel collar after a dose of a medicament contained in the pre-filled syringe has been disposed beneath the skin of a patient receiving the injection. The pivoting arm locks the pre-filled syringe to the support body, so that the pre-filled syringe may be retracted with respect to the needle shield by a proximal movement of the support body with respect to the needle shield.

The pivoting arm is integrally moulded to the support body and connected thereto by a living hinge. The living hinge is essentially formed by a section of reduced wall thickness formed into support body's lateral wall. The support body, the outer body and the needle shield are made from a plastics material, like a polyethylene or a polypropylene, in particular by means of injection moulding. The living hinge is particularly inexpensive to manufacture and provides a flexible feature used for a safety mechanism of the safety device to prevent accidental needle stick injuries after the injection is completed.

The low production cost of the safety device allows for the utilization of the safety device as a single-use device that is disposed after the injection is performed.

According to one possible embodiment of the invention, the support body comprises a first clip adapted to attach a plunger of the pre-filled syringe to the support body. The plunger is connected to a stopper fluid tightly sealing a barrel of the pre-filled syringe. The support body may be translated in the distal direction to depress the plunger into the barrel to expel the dose of the medicament through the injection needle. The outer body is arranged to abut against the support body, so that the support body and the plunger connected thereto may be translated in the distal direction by manually pushing the outer body in the distal direction.

According to another possible embodiment of the invention, the second clip of the outer body latches to the needle shield to prevent a translation of the outer body relative to the needle shield. The needle shield is adapted to rest on the skin of the patient during the injection and is translated in a proximal direction to insert the injection needle into the skin of the patient. The second clip initially affixes the needle shield to the outer body and hence prevents an inadvertent exposure of the injection needle until a release element of the outer body is manually actuated. The release element may in particular be arranged to a lateral wall of the outer body as a push button. Manual actuation of the release element deflects the second clip radially outwards, whereby the second clip unlatches from the needle shield as to allow for a translation of the outer body relative to the needle shield. The user of the device thus has to perform to two separate actions to insert the injection needle into the skin of the patient: the release element is manually actuated and, subsequently, the outer body is pushed in the distal direction. This minimizes the risk of inadvertently exposing the injection needle and hence minimizes the risk of a needle stick injury.

According to yet another possible embodiment of the invention, a first notch and a second notch is formed to an outer surface of the support body. The outer body comprises a third clip that is arranged to protrude into the first notch to retain the support body with respect to the outer body in a first position. The support body is initially retained in the first position, wherein the support body is spaced apart from a proximal end wall of the outer body. Hence, the outer body must be pushed in the distal direction by a distance before the end wall abuts against the support body. The support body and the pre-filled syringe coupled thereto may then be translated by the distal translation of the outer body to insert the injection needle into the skin of the patient. The third clip is arranged to protrude into a second notch to retain the support body with respect to the outer body in a second position. The support body in the second position abuts against the outer body in the proximal direction, so that outer body and support body may jointly move in the distal direction to insert the injection needle into the skin of the patient. Hence, the user needs to translate the outer body with respect to the support body by a minimal axial distance, whereby the support body is translated from the first to the second position, before the injection needle is moved distally. This avoids an unintentional exposure of the injection needle, so that needle stick injuries may be avoided.

In yet another possible embodiment of the invention, the first inner sleeve of the outer body is arranged to abut on the support body in a radial direction. The support body is arranged to slide into the first inner sleeve when the outer body pushed in the distal direction. The first sleeve guides the movement of the support body and prevents that support body gets jammed or stuck in particular during the needle insertion phase of the injection.

According to the invention, an injection device comprises a safety device and a pre-filled syringe with an injection needle. The safety device comprises a needle shield adapted to cover the injection needle of the pre-filled syringe before and after an injection, a support body with at least one pivoting arm adapted to engage a barrel collar of the pre-filled syringe, an outer body with a first inner sleeve comprising a bevelled section.

The needle shield, the support body and the outer body are telescopically arranged. The needle shield, the support body and the outer body may telescope to cover and to expose the injection needle during the injection. The bevelled section is arranged to abut against the pivoting arm connected to the support body by a living hinge to deflect the pivoting arm radially inwards, so that the pivoting arm may engage the barrel collar after a dose of a medicament contained in the pre-filled syringe has been disposed beneath the skin of a patient receiving the injection. The pivoting arm locks the pre-filled syringe to the support body, so that the pre-filled syringe may be retracted with respect to the needle shield by a proximal movement of the support body with respect to the needle shield.

The injection device comprising the pre-filled syringe and the safety device combines the aforementioned advantages and prevents inadvertent needle sticks injuries. The injection device is inexpensive to manufacture and is disposed after a single injection has been carried out.

According to one possible embodiment of the invention, the pre-filled syringe comprises a plunger firmly attached to the support body by a first clip as to allow for a joint translation of the pre-filled syringe and the support body with respect to the needle shield. The pre-filled syringe is arranged to be moved from an initial refracted position, in which the injection needle is covered by the needle shield, to an advanced position, in which the injection needle protrudes from the needle shield in the distal direction.

According to another possible embodiment of the invention, a non-energized or only slightly energized compression spring biases the needle shield and the outer body away from each other. The compression spring is compressed and energized during use of the injection device, wherein the energized compression spring is capable of retracting the pre-filled syringe to cover the injection needle after the dose of the medicament has been disposed beneath the skin of the patient receiving the injection. The arrangement of the compression spring in a non-energized or only slightly energized state avoids material fatigue. This ensures an extended shelf-life of the injection device. The injection device works reliably even after prolonged periods of storage.

In one embodiment of the invention, the inwardly deflected pivoting arm is arranged to engage a barrel collar to lock the pre-filled syringe to the support body after the injection of the medicament. The injection device is thus effectively prevented from being re-used. Furthermore, the pre-filled syringe may be retracted to cover the injection needle by a proximal translation of the support body.

According to another possible embodiment of the invention, the compression spring is capable of driving the pre-filled syringe locked to the support body from the advanced position to a safe position. The needle shield surrounds the pre-filled syringe in the safe position to prevent needle stick injuries after the injection device has been used. A third clip of the outer body protrudes into a second notch formed into the support body to lock the outer body to the support body. The compression spring is charged during the injection and drives the support body, the outer body and the pre-filled syringe that are locked together in the proximal direction to render the injection device needle safe and non-reusable.

According to yet another possible embodiment of the invention, the needle shield comprises a second inner sleeve that comprises an inner diameter corresponding to an outer diameter of the syringe barrel. The pre-filled syringe is slidably retained within the second inner sleeve so as to guide the translation of the pre-filled syringe from the retracted to the advanced and further to the safe position, so that the risk of a malfunction resulting from the pre-filled syringe getting stuck or jammed during translation is minimized.

The pre-filled syringe may be filled with a medicament.

The term "medication", or "drug", or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬ decanoyl)human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
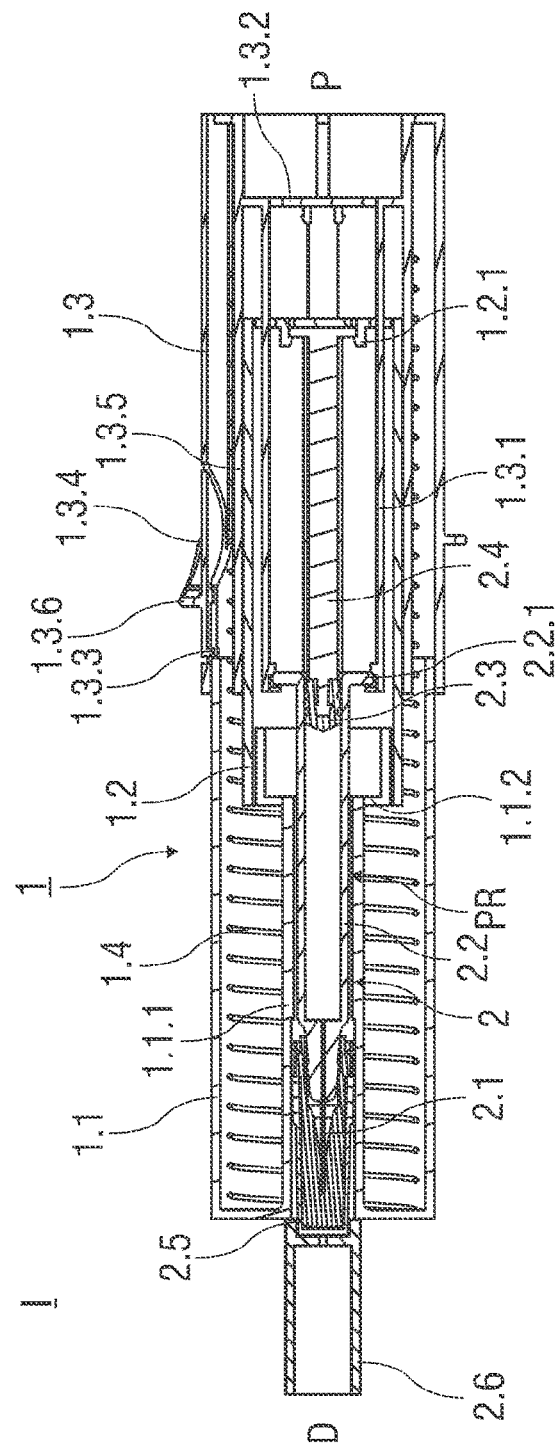
FIG. 1 shows a sectional view of an injection device comprising a safety device and a pre-filled syringe in a packaged state.

FIG. 1 shows a sectional view of an injection device I comprising a safety device 1 and a pre-filled syringe 2 retained therein as it would be presented to a user performing an injection. The safety device 1 comprises a substantially cylindrical and hollow needle shield 1.2, a substantially cylindrical and hollow support body 1.2 and a substantially cylindrical and hollow outer body 1.3 with a closed distal end. The needle shield 1.1, the support body 1.2 and the outer body 1.3 fit into each other and are arranged so as to telescope with respect to each other during an injection, so that an injection needle 2.1 of the pre-filled syringe may be exposed and inserted into the skin of a patient receiving an injection and covered after the injection delivering a dose of a medicament has been completed.

Initially, the pre-filled syringe 2 is retained within the safety device 1 in a retracted position PR, wherein the injection needle 2.1 is covered by the needle shield 1.1. The pre-filled syringe 2 is releasably mounted to the outer body 1.3, so that the pre-filled syringe 2 may be translated in a distal direction D by manually translating the outer body 1.3 with respect to the needle shield 1.1 in the distal direction D. Two elongated latch arms 1.3.1 are formed to an inner surface of the outer body 1.3 that latch to barrel collar 2.2.1 of a syringe barrel 2.2 containing the dose of the medicament. The two latch arms 1.3.1 are arranged opposite to each other and are made from a resilient plastics material as to allow for a splaying of the latch arms 1.3.1 to release the pre-filled syringe 2 from being affixed to the outer body 1.3.

A stopper 2.3 connected to a plunger 2.4 liquid tightly seals a distal end of the syringe barrel 2.2. The stopper 2.3 may be translated in the distal direction D by depressing the plunger 2.4 into to syringe barrel 2.2, whereby the dose of the medicament is expelled through the injection needle 2.1. The plunger 2.4 is firmly attached to the support body 1.2 by first clips 1.2.1 that latch to a proximal end of the plunger 2.4. An end wall 1.3.2 of the outer body 1.3 is arranged to bear against the support body 1.2 to push the support body 1.2 and the plunger 2.4 connected thereto in the distal direction D, so that the stopper 2.3 is translated distally to expel the dose of the medicament.

Before the injection, a translation of the needle shield 1.1 relative to the outer body 1.3 is prevented by a second clip 1.3.3 formed to the distal end of the outer body 1.3. The second clip 1.3.3 initially latches to a proximal end of the needle shield 1.1 and may be released by manually pushing a release element 1.3.4 formed to a lateral side wall of the outer body 1.3 radially inwards, whereby the second clip 1.3.3 is deflected radial outwards to disengage from the proximal end of the needle shield 1.1.

A compression spring 1.4 is arranged within the safety device 1 that biases the needle shield 1.1 and the outer body 1.3 away from each other. Initially, the compression spring 1.4 is in a non-energized or only slightly energized state. The compression spring 1.4 is compressed and energized during the injection when the outer body 1.3 is translated with respect to the needle shield 1.1 in the distal direction D. The energized compression spring 1.4 is capable of retracting the pre-filled syringe 2 to cover the injection needle 2.1 after the dose of the medicament has been expelled.

The outer body 1.3 comprises a first inner sleeve 1.3.5 that is dimensioned to slide over the substantially tubular support body 1.2 when the outer body 1.3 is manually pushed in the distal direction D to insert the injection needle 2.1 and to expel the dose of the medicament through the injection needle 2.1.

The needle shield 1.1 comprises a second inner sleeve 1.1.1 that has an inner diameter corresponding to an outer diameter of the syringe barrel 2.2. The pre-filled syringe 2 is inserted into the second inner sleeve 1.1.1 and is slidably arranged thereto. The pre-filled syringe 2 is arranged to be translated from the retracted position PR shown in FIG. 1 in the distal direction D to expose the injection needle 2.1. A shoulder 1.1.2 is formed to the second inner sleeve 1.1.1 that is arranged to abut against the barrel collar 2.2.1 to limit the distal displacement of the pre-filled syringe 2 with respect to the needle shield 1.1.

In the packaged state shown in FIG. 1, a needle cap 2.5 is frictionally affixed to a distal end of the pre-filled syringe 2.2 to cover the injection needle 2.1. The needle cap 2.5 is substantially retained within the second inner sleeve 1.1.1 of the needle shield 1.1. A tubular cap removal tool 2.6 is arranged to clamp to a distal end of the needle cap 2.2. The removal tool 2.6 protrudes from the needle shield 1.1 in the distal direction and may easily be gripped and pulled by a user of the injection device I to facilitate the removal of the needle cap 2.2 before the injection is carried out.

Alternatively, the removal tool 2.6 may be integral with the needle cap 2.5 or the needle cap 2.5 may have axial dimensions and may be arranged with respect to the needle shield 1.1, so that the needle cap 2.2 partially protrudes distally from the needle shield 1.1 and may be gripped and removed by the user.

Figure 2:
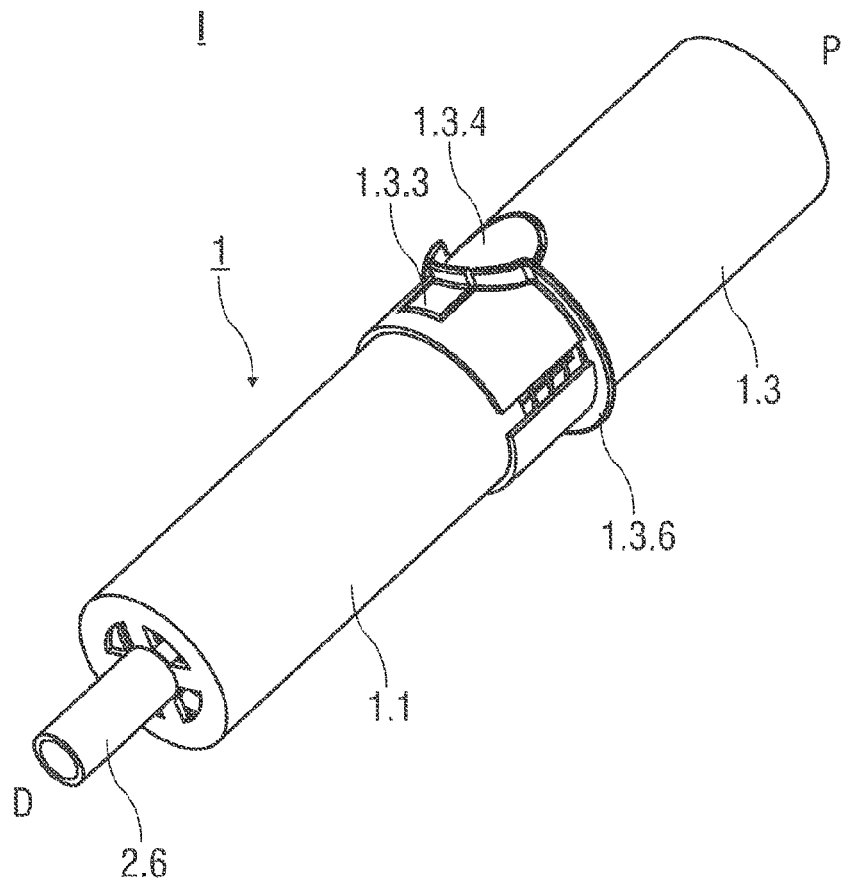
FIG. 2 shows an isometric view of the injection device before use.

FIG. 2 shows the injection device I before use in an isometric view. A circumferential flange 1.3.5 is formed to an outer surface of the outer body 1.3 that protrudes from the outer body 1.3 in the radial outward direction. The flange 1.3.5 is designed to support a hand of the user of the injection device I when a proximal section of the outer body 1.3 is gripped by the user to push the outer body 1.3 in the distal direction D in order to insert the injection needle 2.1 into the skin of the patient and dispose the dose of the medicament.

Figure 3A:
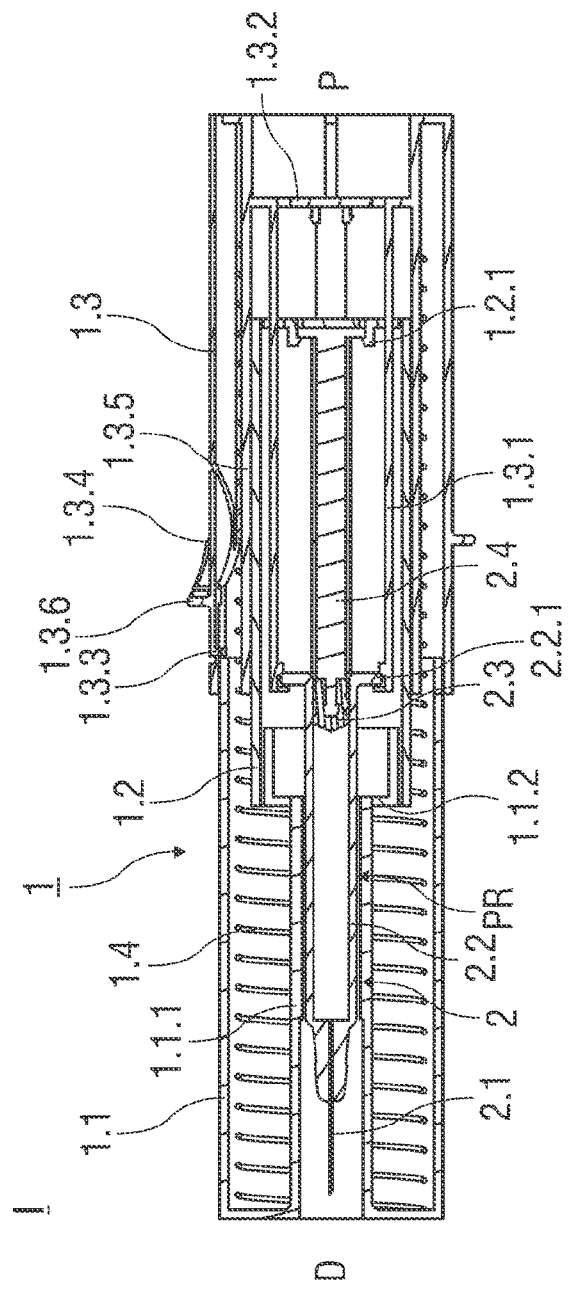
FIGS. 3A and 3B show the injection device after removal of a needle cap and before an injection is performed.
Figure 3B:
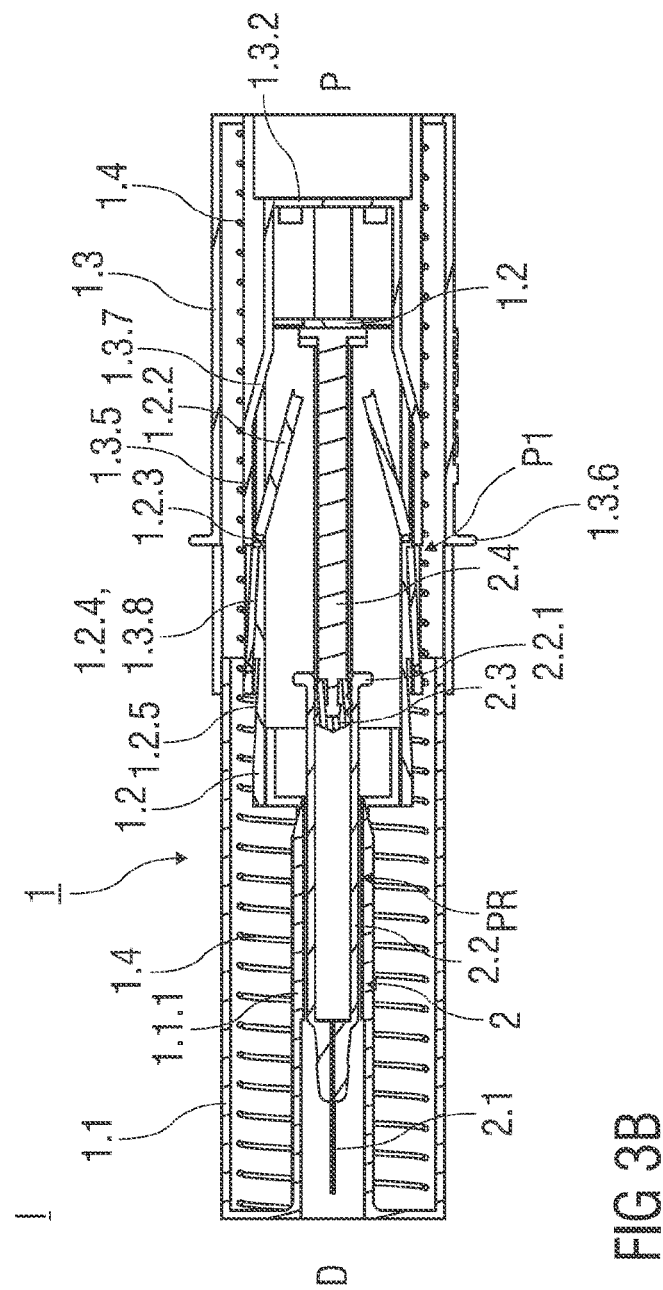

FIGS. 3A and 3B show the injection device I after removal of the needle cap 2.6 and before the injection is performed. The sectional plane shown in FIG. 3A extends perpendicularly to the one shown in FIG. 3B.

The first inner sleeve 1.3.5 comprises a bevelled section 1.3.7 that is arranged to abut against a pivoting arm 1.2.2 arranged with the support body 1.2 as one piece. The pivoting arm 1.2.2 is connected to the support body 1.2 by a section of reduced wall thickness that forms a so-called living hinge 1.2.3. Two pivoting arms 1.2.2 are arranged opposite to each other. The pivoting arms 1.2.2 may pivot about the living hinge 1.2.3 to constrict radially inwards and latch to the barrel collar 2.2.1 to permanently lock the pre-filled syringe 2 to the support body 1.2 after the dose of the medicament has been expelled.

A third clip 1.3.8 is formed to the first inner sleeve 1.3.5 of the outer body 1.3 near its distal end. The third clip 1.3.8 protrudes into a correspondingly shaped first notch 1.2.4 formed to an outer surface of the support body 1.2 to retain the support body 1.2 with respect to the outer body 1.1 in a first position P1. In the first position P1, the support body 1.2 is spaced away from the end wall 1.3.2 of the outer body 1.3. The first notch 1.2.4 comprises a ramped surface that allows the support body 1.2 to be moved with respect to the outer body in a proximal direction P. A second notch 1.2.5 is formed to the outer surface of the support body 1.2 that is arranged to be engaged by the third clip 1.3.8 to retain the support body 1.2 in a second position P2, wherein the support body 1.2 is substantially received within the outer body 1.3 and abuts against the end wall 1.3.2 in the proximal direction P.

The injection is carried out as follows: after removal of the needle cap 2.5, the injection device I is arranged in a manner, so that the distal end of the needle shield 1.1 rests on the skin of the patient. The proximal end of the outer body 1.3 is gripped by the user and the release element 1.3.4 that is designed as a push button is pressed radially inwards to release the second clip 1.3.3, so that the outer body 1.3 may be pushed in the distal direction D towards the skin of the patient. Upon translation of the outer body 1.3 in the distal direction D, the support body 1.2 first slides into the first inner sleeve 1.3.5 of the outer body 1.3, whereby the pivoting arm 1.2.2 engages the bevelled section 1.3.7 to deflect the pivoting arm 1.2.2 radial inwards. At the same time, the needle shield 1.1 slides into the outer body 1.3 and the compression spring 1.4 is gradually compressed and energized.

The outer body 1.3 is pushed further in the distal direction D until the proximal end wall 1.3.2 abuts on the support body 1.2 arranged in the second position P2. A further distal translation of the outer body 1.3 thus translates the support body 1.2 and the pre-filled syringe 2 connected thereto in the distal direction D to insert the injection needle 2.1 into the skin of the patient. The needle shield 1.1 slides further into the outer body 1.3 until the pre-filled syringe 2 reaches—relative to the needle shield 1.1—an advanced position PA shown in FIG. 4.

Figure 4:
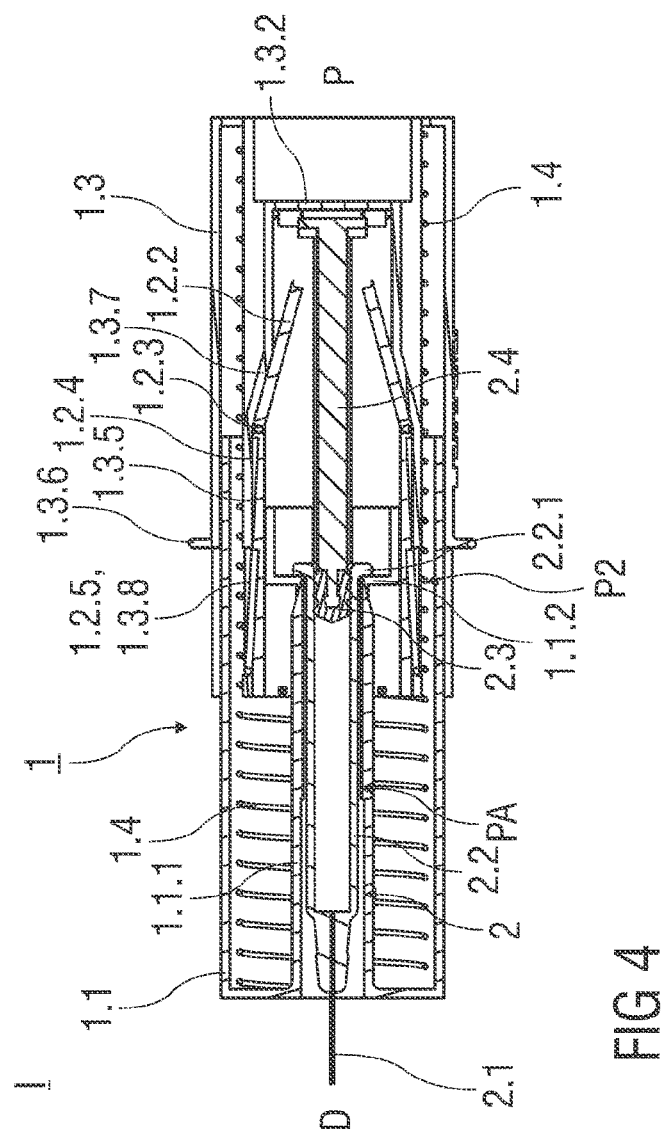
FIG. 4 shows a sectional view of the injection device with the pre-filled syringe arranged in an advanced position.

FIG. 4 shows a sectional view of the injection device I with the pre-filled syringe 2 arranged in the advanced position PA. The injection needle 2.1 protrudes from the distal end of the needle shield 1.1 and penetrates the skin of the patient receiving the injection. The pivoting arm 1.2.2 abuts on the bevelled section 1.3.7 and is deflected in the radial inward direction. The barrel collar 2.2.1 abuts against the shoulder 1.1.2 formed to the second inner sleeve 1.1.1 of the needle shield 1.1 to limit the distal displacement of the pre-filled syringe 2 with respect to the needle shield 1.1.

A further movement of the outer body 1.3 in the distal direction D deflects the latch arms 1.3.1, whereby the latch arms 1.3.1 disengage form the barrel collar 2.2.1. Furthermore, the engagement of the barrel collar 2.2.1 with the shoulder 1.1.2 limits a penetration depth of the injection needle 2.1 into the skin of the patient.

According to possible embodiments of the invention, the penetration depth may be adjusted to a subcutaneous, an intramuscular or an intradermal injection of the dose of the medicament contained in the pre-filled syringe 2.

The support body 1.2 is substantially received within the outer body 1.3. The third clips 1.3.8 latch into the second notches 1.2.5 to lock the outer body 1.3 and the support body 1.2 together and hence prevent a translation of the outer body 1.3 relative to the support body 1.2 in the distal direction D.

The outer body 1.3 is pushed further in the distal direction D towards the skin of the patient. The support body 1.2 and the plunger 2.4 connected thereto are translated in the distal direction D, whereby the plunger 2.4 depresses into the syringe barrel 2.2 and pushes the stopper 2.3 distally to inject the dose of the medicament.

Figure 5:
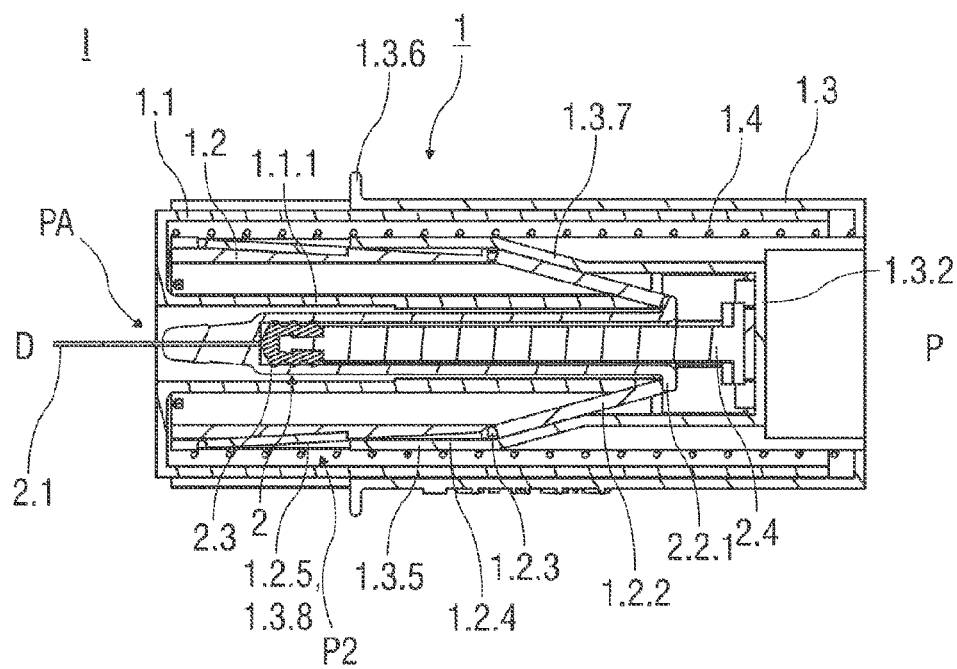
FIG. 5 shows a sectional view of the injection device at the end of an injection stroke.

At the end of the injection stroke, the stopper 2.3 bottoms out and reaches a distal end of the syringe barrel 2.2 as shown in FIG. 5.

FIG. 5 shows a sectional view of the injection device I at the end of the injection stroke. The dose of the medicament has been completely expelled. The needle shield 1.1 is substantially received within the hollow outer body 1.3. The pivoting arms 1.2.2 constrict radially inwards and engage the barrel collar 2.2.1. The pre-filled syringe 2 is now locked to the support body 1.2 which is affixed to the outer body 1.3 by the third clips 1.3.8 engaging the second notch 1.2.4. Upon removal of the injection device I from the injection site, the outer body 1.3 and the pre-filled syringe 2 connected thereto is driven in the proximal direction P towards a safe position PS by the energized compression spring 1.4.

Figure 6A:
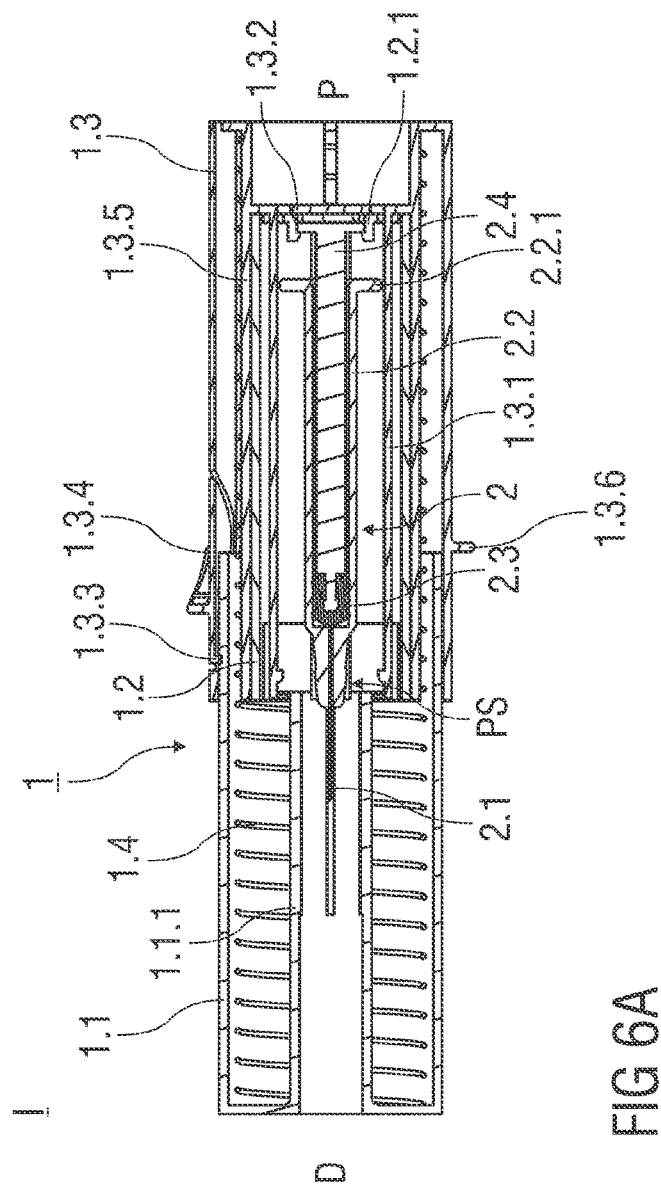
FIGS. 6A and 6B show sectional views of the injection device in a needle safe state after the injection has been completed.
Figure 6B:
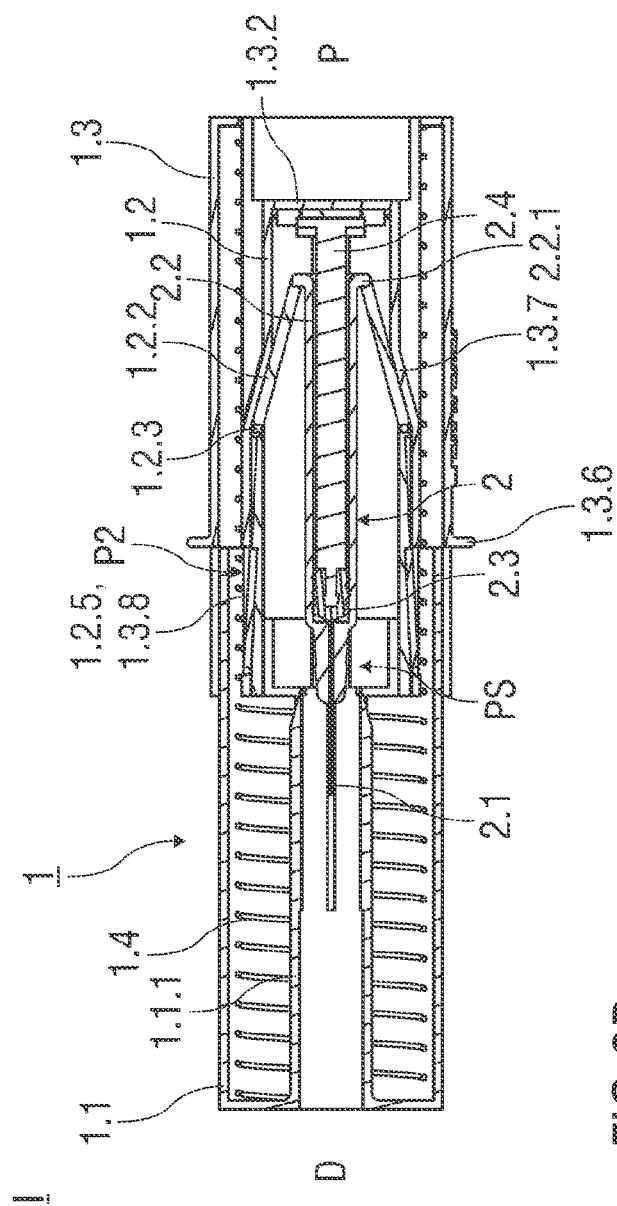

FIGS. 6A and 6B show sectional views of the injection device I after the injection is completed. The pre-filled syringe 2 is retracted within the safety device 1 in a safe position PS. The needle shield 1.1 covers the injection needle 2.1 to prevent accidental needle stick injuries.

The second clip 1.3.3 latches to the needle shield 1.1 to lock the needle shield 1.1 with respect to the pre-filled syringe 2 in the safe position PS after the injection is completed, so that a subsequent re-exposure of the injection needle 2.1 is prevented.

A subsequent actuation of the release element 1.3.4 may release the second clip 1.3.3 to allow for a proximal movement of the needle shield 1.1 with respect to the pre-filled syringe 2 re-exposing the injection needle 2.1.

The invention claimed is:

1. Safety device for a pre-filled syringe comprising:
a needle shield adapted to cover an injection needle of the pre-filled syringe before and after an injection;
a support body with at least one pivoting arm adapted to engage a barrel collar of the pre-filled syringe;
an outer body with a first inner sleeve comprising a bevelled section, the outer body arranged to be releasbly mounted to the pre-filled syringe, so that the pre-filled syringe may be translated in a distal direction by manually translating the outer body with respect to the needle shield in the distal direction; and
a compression spring arranged within the safety device that biases the needle shield and the outer body away from each other;
wherein the needle shield, the support body and the outer body are arranged so as to telescope with respect to each other between a first position (P1) and a second position (P2), wherein the support body in the first position (P1) is spaced apart from an end wall of the outer body and wherein the support body in the second position (P2) abuts against the end wall in a proximal direction (P), and wherein, in the second position (P2) after the dose of the medicament has been expelled, the bevelled section abuts against the pivoting arm connected to the support body by a living hinge deflecting the pivoting arm radially inwards thereby latching the pivoting arm to the barrel collar and permanently locking the pre-filled syringe to the support body.

2. Safety device according to claim 1, characterized in that the support body comprises a first clip adapted to attach a plunger of the pre-filled syringe to the support body.

3. Safety device according to claim 1, characterized in that a second clip of the outer body latches to the needle shield to prevent a translation of the outer body relative to the needle shield and wherein the outer body comprises a release element that is arranged to be manually actuated to deflect the second clip radially outwards to allow for a translation of the outer body relative to the needle shield.

4. Safety device according to claim 1, characterized in that the support body comprises a first notch and a second notch and the outer body a third clip that is arranged to protrude into the first notch to retain the support body with respect to the outer body in the first position (P1) and wherein the third clip is arranged to protrude into the second notch to retain the support body with respect to the outer body in the second position (P2).

5. A safety device according to claim 1, characterized in that the first inner sleeve of the outer body arranged to abut on the support body in a radial direction.

6. Injection device (I) comprising a safety device according to claim 1 and a pre-filled syringe with an injection needle.

7. Injection device (I) according to claim 6, characterized in that the pre-filled syringe comprises a plunger firmly attached to the support body by a first clip as to allow for a joint translation of the pre-filled syringe and the support body with respect to the needle shield from a retracted position (PR) to an advanced position (PA), wherein the injection needle in the retracted position (PR) is covered by the needle shield and wherein the injection needle in the advanced position (PA) protrudes from the needle shield in the distal direction (D).

8. Injection device (I) according to claim 6, characterized in that a non-energized or only slightly energized compression spring biases the needle shield and the outer body away from each other.

9. Injection device (I) according to claim 6, characterized in that the inwardly deflected pivoting arm is arranged to engage a barrel collar to lock the pre-filled syringe to the support body.

10. Injection device (I) according to claim 9, characterized in that the compression spring is capable of driving the pre-filled syringe locked to the support body from the advanced position (PA) to a safe position (PS), wherein a third clip of the outer body protrudes into a second notch to lock the outer body to the support body.

11. Injection device (I) according to claim 5, characterized in that the needle shield comprises a second inner sleeve that comprises an inner diameter corresponding to an outer diameter of the syringe barrel.

* * * * *